(12) United States Patent
Finson

(10) Patent No.: US 10,189,792 B2
(45) Date of Patent: Jan. 29, 2019

(54) METHOD AND APPARATUS FOR SYNTHESIZING A WATER-SOLUBLE HEXAARYL BIIMIDAZOLE

(71) Applicant: Stephen L Finson, West Haven, CT (US)

(72) Inventor: Stephen L Finson, West Haven, CT (US)

(*) Notice: Subject to any disclaimer, the term of this patent is extended or adjusted under 35 U.S.C. 154(b) by 54 days.

(21) Appl. No.: 15/453,519

(22) Filed: Mar. 8, 2017

(65) Prior Publication Data

US 2018/0258051 A1    Sep. 13, 2018

(51) Int. Cl.
*C07D 233/64*    (2006.01)
*G03F 7/031*    (2006.01)

(52) U.S. Cl.
CPC .......... *C07D 233/64* (2013.01); *G03F 7/031* (2013.01)

(58) Field of Classification Search
CPC .............................. C07D 233/64; G03F 7/031
See application file for complete search history.

(56) References Cited

U.S. PATENT DOCUMENTS 3,666,466 A * 5/1972 Strilko ................ C07D 233/64
430/333

OTHER PUBLICATIONS

Research Disclosure (Mar. 10, 1996), 383, 161-162, No. 383009, (RD 383009).*
Cescon et al., Journal of Organic Chemistry, vol. 36, No. 16, pp. 2262-2267.*

* cited by examiner

*Primary Examiner* — Laura L Stockton
(74) *Attorney, Agent, or Firm* — Gilbride, Tusa, Last & Spellane, LLC.; Todd S. Sharinn

(57) ABSTRACT

A method for forming a water-soluble hexaaryl biimidazole, comprising the steps of reacting benzil with a carboxy benzaldehyde and ammonium acetate to yield a carboxy triaryl imidazole, and dimerizing the carboxy triaryl imidazole in an alkaline aqueous solution of potassium ferricyanide to yield a water-soluble salt of a bicarboxy hexaaryl biimidazole.

4 Claims, 3 Drawing Sheets

METHOD AND APPARATUS FOR SYNTHESIZING A WATER-SOLUBLE HEXAARYL BIIMIDAZOLE

TECHNICAL FIELD

The present invention relates to synthesis of organic compounds; more particularly, to synthesis of photo-initiators; and most particularly to a method and apparatus for synthesizing a water-soluble hexaaryl biimidazole (also referred to herein as "HABI").

BACKGROUND OF THE INVENTION

Various derivatives of hexaaryl biimidazole are well known in the prior art as radical polymerization photoinitiators. All such photoinitiators are insoluble in water.

For example, U.S. Pat. No. 6,524,770 B1, "Hexaaryl biimidazole compounds as photoinitiators, photo sensitive composition and method of manufacturing patterns using the compounds", issued Feb. 25, 2003 to Hidaka et al. and incorporated herein by reference in its entirety discloses a hexaaryl biimidazole compound useful as a photoinitiator, represented by Formula (I) shown in FIG. 1, wherein each R group represents an alkyl group which may be the same or different, and each X group is independently a fluorine or hydrogen. The compound (I) is particularly useful as an initiator in a photosensitive composition containing a polyimide precursor, which is curable under patternwise low radiation exposure to give a patterned layer having heat and chemical resistance.

For further example, U.S. Pat. No. 7,901,501 B2, "Ink jet composition", issued Mar. 8, 2011 to Kobayashi, discloses an inkjet ink composition comprising: a white pigment; a polymerizable compound; and a polymerization initiator. The white pigment includes at least one of inorganic hollow particles or inorganic-organic hybrid hollow particles. The polymerization initiator may be a hexaaryl biimidazole.

In the prior art, hexaaryl biimidazoles (HABI) typically are manufactured in multiple steps. The first step involves the condensation of a benzaldehyde and a benzil, which may be substituted, with ammonium acetate in refluxing acetic acid to form a triaryl imidazole monomer comprising first, second, and third phenyl rings as shown in FIG. 1. The HABI dimer is then formed through oxidative coupling of the corresponding monomer. Both the benzaldehyde and benzil can be substituted at the various ring positions to give the HABI dimer specific characteristics such as improved solubility or photospeed.

U.S. Pat. No. 3,784,557, issued Jan. 8, 1974 to Cescon ("Cescon") and incorporated by reference herein in its entirety discloses 2,4,5-triphenylimidazolyl radicals and their dimers (2,2',4,4',5,5' hexaphenyl biimidazoles) having on the phenyl groups from 1 to 10 substituents free from a hydrogen atom capable of reacting with methyl magnesium iodide, one such substituent being in the ortho position on the 2-phenyl group and having a sigma value below 0.7. The 2-phenyl group can contain up to four substituents, while the 4 and 5 phenyl groups can contain up to three substituents each. The radicals and the dimers are stable and form a photochromic system, finding utility as components in sun shields or shades. They are prepared by oxidizing the corresponding substituted 2,4,5-triaryl imidazole to form the hexaaryl biimidazole which is dark stable. The radical forms upon exposure of the biimidazole to a light source and is stable in the presence of the light radiation.

Cescon does not disclose synthesis of carboxy-substituted hexaaryl diimidazoles and in fact teaches away from substituent groups comprising hydroxyl, thio, carboxyl, amino, and alkylamino. Surprisingly, it has now been found that a carboxy-substituted triaryl imidazole can be a useful intermediate in forming a water-soluble HABI salt in accordance with the present invention.

Cescon does disclose to perform the dimerization in the presence of an ethanol solution of an alkali, specifically KOH, but because the carboxy substituent is not taught in the disclosure and because the solvent is not water, the present invention is not anticipated.

In the prior art, all known HABI compounds are essentially water-insoluble, requiring the use of organic and/or other non-polar solvents to form solutions thereof, which places limitations on useful formulations of HABI compounds.

What is needed in the art are HABI compounds that are inherently water-soluble, e.g., salts of carboxylated HABI compounds.

SUMMARY OF THE INVENTION

Briefly described, an exemplary carboxylated triaryl imidazole is formed by reacting benzil (dibenzoyl) with carboxy benzaldehyde in the presence of ammonium acetate in acetic acid. The resulting carboxy triaryl imidazole is then dimerized in an aqueous solution of potassium ferricyanide and an alkali to yield the alkali salt of a bicarboxy hexaaryl biimidazole, which is crystallized from solution. In a currently-preferred embodiment, the preferred precursor is 2-carboxy benzaldehyde and the preferred alkali is NaOH, which yields the preferred dimer of the disodium salt of 2,2'-bicarboxy hexaaryl biimidazole.

BRIEF DESCRIPTION OF THE DRAWINGS

The present invention will now be described, by way of example, with reference to the accompanying drawings, in which:

FIG. 2b is a structural chemical drawing showing a carboxylated triaryl imidazole compound produced by the reaction shown in FIG. 2a.

DESCRIPTION OF THE PREFERRED EMBODIMENTS

Figure 1:
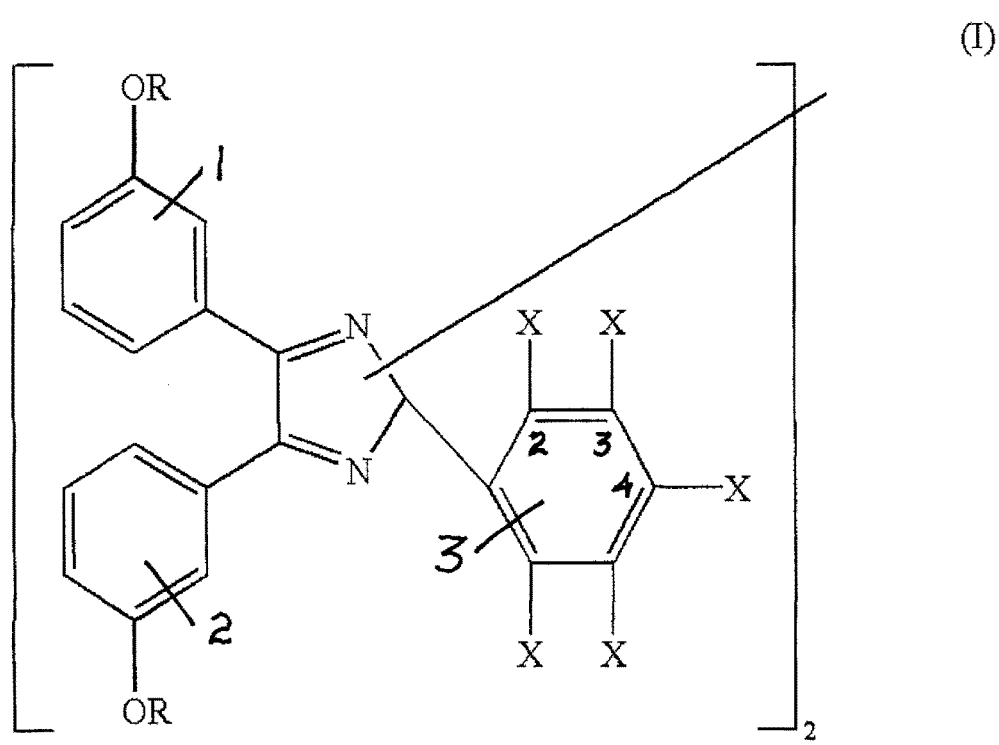
FIG. 1 is a structural chemical drawing of a prior art generic hexaaryl biimidazole compound.
Figure 2A:
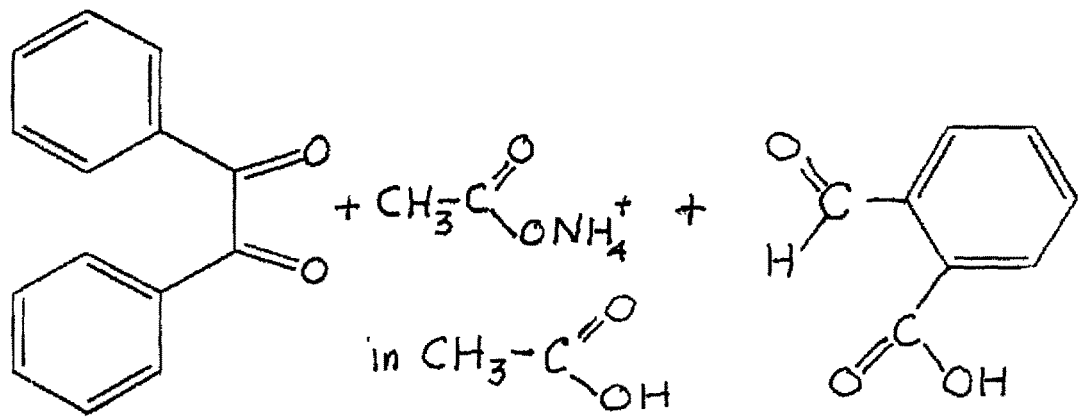
FIG. 2a is a structural chemical drawing showing an exemplary reaction for forming a carboxylated triaryl imidazole compound by reacting benzil (dibenzoyl) with carboxy benzaldehyde in the presence of ammonium acetate in acetic acid.
Figure 2B:
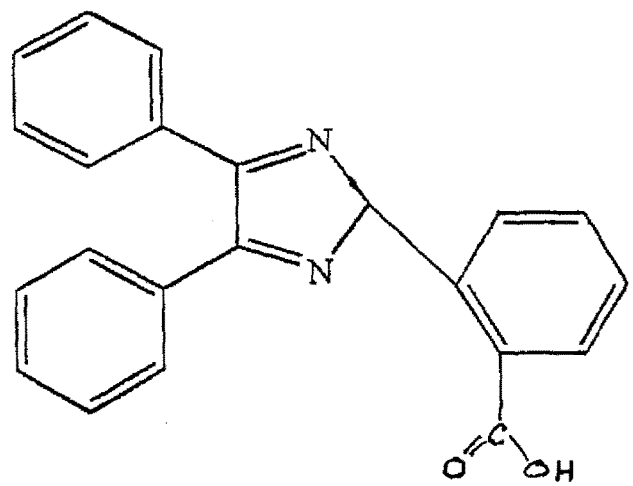

Referring now to FIGS. 2a,2b, a carboxylated triaryl imidazole monomer is formed by reaction of benzil and a carboxy benzaldehyde in the presence of ammonium acetate and acetic acid, which carboxylation may be selected at the 2, 3, or 4 position of the benzaldehyde ring. The 2-position is currently preferred.

Example 1

In a reaction vessel equipped with a stirrer and condenser, 80 parts (0.38 moles) by mass of benzil was combined with 60 parts (0.40 moles) by mass of 2-carboxy benzaldehyde and 108 parts (1.40 moles) by mass of ammonium acetate in 350 ml of glacial acetic acid. The mixture was heated to reflux for 8 hours. After cooling, 400 ml of water was added and stirred at room temperature. A precipitate of 2-carboxy triaryl imidazole was recovered by filtration and dried.

Figure 3:
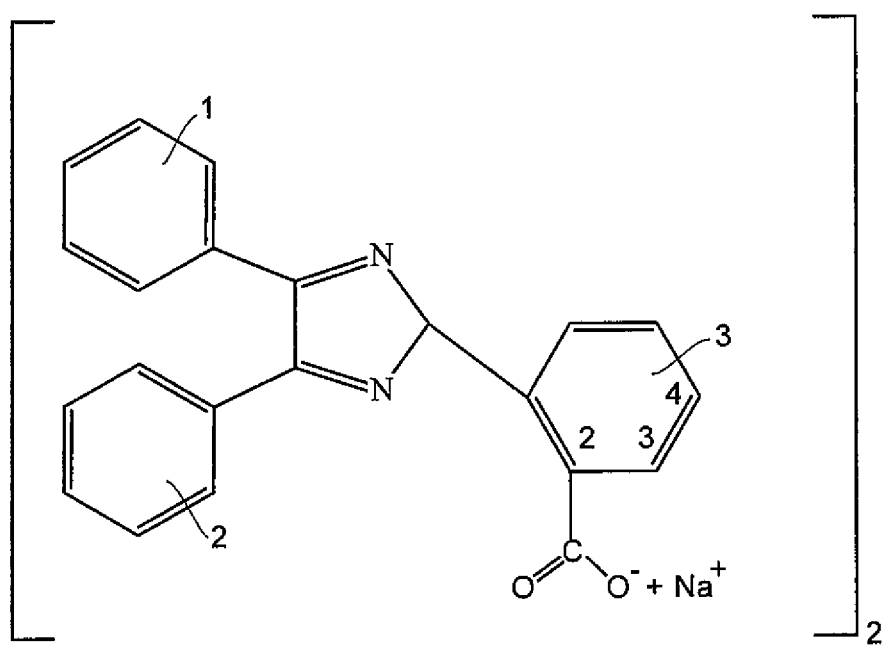
FIG. 3 is a water-soluble hexaaryl biimidazole compound in accordance with the present invention.

Referring now to FIG. 3, carboxy triaryl imidazole is dimerized in an aqueous solution of potassium ferricyanide and an alkali to yield the alkali salt of a bicarboxy hexaaryl biimidazole, which is crystallized from solution by addition of sodium chloride. In a currently-preferred embodiment, the preferred precursor is 2-carboxy benzaldehyde (FIG. 2b) and the preferred alkali is sodium hydroxide, which yields the preferred dimer of the disodium salt of 2,2' bicarboxy hexaaryl biimidazole.

Example 2

In a reaction vessel equipped with a stirrer, 30 parts (0.11 moles) by mass of 2-carboxy triaryl imidazole was combined with 80 parts (0.24 moles) by mass of potassium ferricyanide in 50 ml of 5 N sodium hydroxide, pH 14, in 600 ml of water at a temperature of 25 C. The mixture was allowed to react with stirring for 12 hours. After addition of 15 grams of sodium chloride, a precipitate of sodium 2,2'-bicarboxy hexaaryl biimidazole was recovered by filtration.

While the invention has been described by reference to various specific embodiments, it should be understood that numerous changes may be made within the spirit and scope of the inventive concepts described. Accordingly, it is intended that the invention not be limited to the described embodiments, but will have full scope defined by the language of the following claims.

What is claimed is:

1. A method for forming a water-soluble hexaaryl biimidazole, comprising the steps of:
   a) reacting benzil with a carboxy benzaldehyde and ammonium acetate to yield a carboxy triaryl imidazole; and
   b) dimerizing said carboxy triaryl imidazole in an alkaline aqueous solution of potassium ferricyanide to yield a water-soluble salt of a bicarboxy hexaaryl biimidazole, wherein said water-soluble salt of a bicarboxy hexaaryl biimidazole is the disodium salt of 2,2'-bicarboxy hexaaryl biimidazole.

2. A compound of the following chemical structure wherein each X group is independently selected from the group consisting of an alkali carboxylate or hydrogen, and wherein at least one of said X groups in an alkali carboxylate:

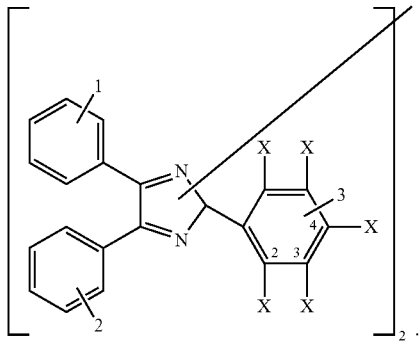

3. A compound having the following chemical structure:

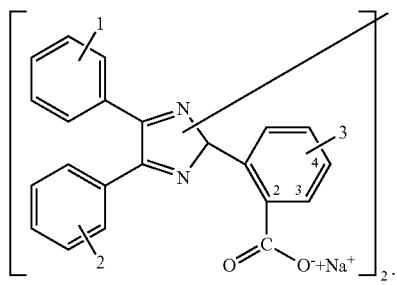

4. A water-soluble hexaaryl biimidazole compound resulting from dimerization of two carboxy triaryl imidazole compounds wherein each of said carboxy triaryl imidazole compounds is an alkali carboxylate isomer.

* * * * *